(12) United States Patent
Bracken

(10) Patent No.: US 8,133,326 B2
(45) Date of Patent: Mar. 13, 2012

(54) ENDOTRACHEAL TUBE CLEANING DEVICES AND METHODS OF REMOVING MUCUS ACCUMULATIONS FROM ENDOTRACHEAL TUBES

(75) Inventor: Ronald L. Bracken, Conyers, GA (US)

(73) Assignee: C.R. Bard, Inc., Murray Hill, NJ (US)

( * ) Notice: Subject to any disclaimer, the term of this patent is extended or adjusted under 35 U.S.C. 154(b) by 428 days.

(21) Appl. No.: 12/353,205

(22) Filed: Jan. 13, 2009

(65) Prior Publication Data

US 2009/0178681 A1    Jul. 16, 2009

Related U.S. Application Data

(60) Provisional application No. 61/020,777, filed on Jan. 14, 2008.

(51) Int. Cl.
*B08B 9/04* (2006.01)
*A61M 16/00* (2006.01)
*A61M 1/00* (2006.01)
*A62B 9/06* (2006.01)

(52) U.S. Cl. ...... 134/8; 134/6; 128/207.14; 128/207.15; 604/317

(58) Field of Classification Search ............ 128/207.15, 128/207.14; 134/6, 8; 604/317
See application file for complete search history.

(56) References Cited

U.S. PATENT DOCUMENTS

| | | | | |
|---|---|---|---|---|
| 3,769,983 | A * | 11/1973 | Merav | 128/207.15 |
| 5,003,657 | A * | 4/1991 | Boiteau et al. | 15/104.33 |
| 5,687,714 | A * | 11/1997 | Kolobow et al. | 128/207.14 |
| 5,709,691 | A * | 1/1998 | Morejon | 606/106 |
| 6,679,262 | B1 * | 1/2004 | Morejon | 128/207.15 |
| 6,986,773 | B1 * | 1/2006 | Manougian | 606/106 |
| 7,338,466 | B2 * | 3/2008 | Hart et al. | 604/93.01 |
| 7,549,419 | B2 * | 6/2009 | Carlsen et al. | 128/201.13 |
| 7,771,346 | B2 * | 8/2010 | Burton et al. | 600/29 |
| 7,854,728 | B2 * | 12/2010 | Boyle, Jr. | 604/267 |
| 2005/0172971 | A1 * | 8/2005 | Kolobow et al. | 128/207.14 |
| 2006/0207602 | A1 * | 9/2006 | Kolobow et al. | 128/207.14 |
| 2006/0207605 | A1 * | 9/2006 | Anderson et al. | 128/207.14 |
| 2006/0264988 | A1 * | 11/2006 | Boyle | 606/159 |
| 2009/0326513 | A1 * | 12/2009 | Deutsch et al. | 604/540 |

* cited by examiner

*Primary Examiner* — Michael Kornakov
*Assistant Examiner* — Katelyn Whatley
(74) *Attorney, Agent, or Firm* — Rutan & Tucker, LLP

(57) ABSTRACT

An endotracheal tube cleaning device may comprise an elongated member, a cleaning member at a first end of the elongated member, and a collection member. The cleaning member may include a shaving region about a periphery thereof. The elongated member may extend through the collection member, and the elongated member and cleaning member may be slidable relative to the collection member.

4 Claims, 2 Drawing Sheets

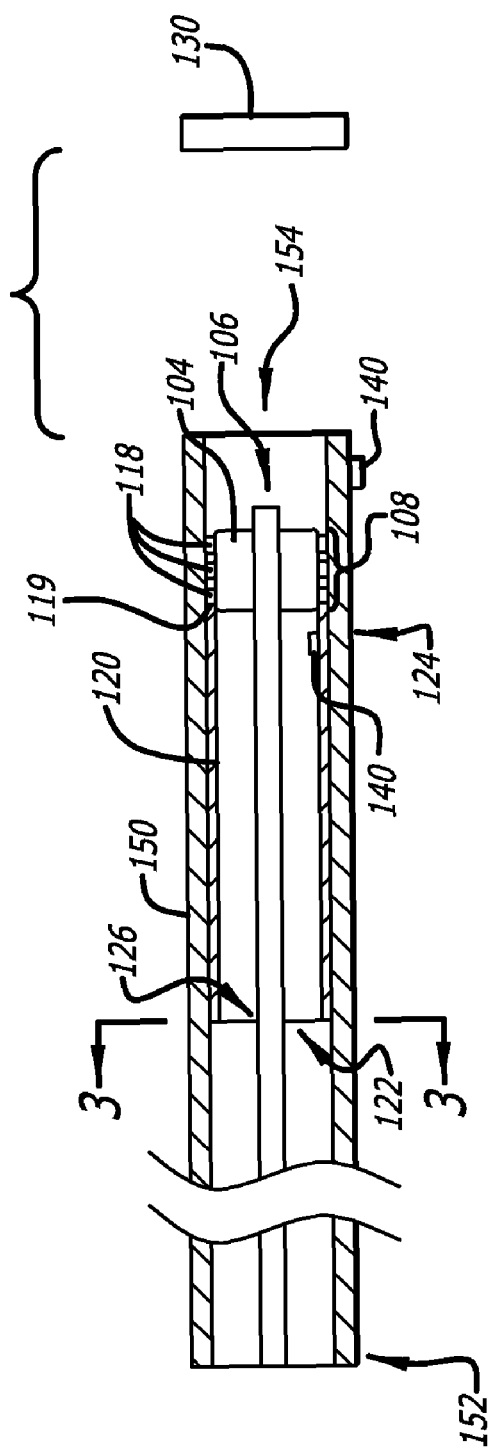

ENDOTRACHEAL TUBE CLEANING DEVICES AND METHODS OF REMOVING MUCUS ACCUMULATIONS FROM ENDOTRACHEAL TUBES

PRIORITY

This application claims the benefit of U.S. Provisional Patent Application No. 61/020,777, filed Jan. 14, 2008, which is incorporated by reference in its entirety into this application.

TECHNICAL FIELD

The present invention is directed to medical devices. More particularly, the present invention is directed to endotracheal tube cleaning devices and methods of removing mucus accumulations from endotracheal tubes.

BACKGROUND

Mechanical ventilation of the lungs of humans and animals is well-known. Such ventilation often involves the introduction of an endotracheal tube into the trachea of an animal, for example, a human.

One problem often encountered with the use of endotracheal tubes is the accumulation of mucus on the inside wall of the endotracheal tube. Several conventional approaches have been employed to address the mucus accumulation problem for endotracheal tubes. One approach is to remove the mucus-laden endotracheal tube from the patient's trachea and replace it with a clean endotracheal tube. Such a procedure can be very uncomfortable for the patient, especially since ventilation must be interrupted during the process. Additionally, frequent reinsertion of a clean endotracheal tube can eventually lead to tracheal injury.

Another conventional approach introduces salt water into the endotracheal tube to dissolve the mucus. The dissolved mucus deposits are then vacuumed with a suction catheter. This approach can be agonizingly long for patients, and it tends to miss a number of the accumulated mucus deposits, thereby leaving them as a breeding ground for infectious bacteria.

Some conventional cleaning apparatuses are also used for cleaning an endotracheal tube (see, e.g., U.S. Pat. Nos. 5,709,691; 6,082,361; 6,318,368, 6,494,208 and 6,679,262 and U.S. Patent Publication No. 2005/0172971, the disclosures of which are all incorporated by reference herein.). When these devices are used to clean an endotracheal tube and subsequently withdrawn from the tube, the removed mucus is exposed on the apparatus and must be removed, for example, via a napkin, by the physician or other practitioner.

It may be desirable to provide an endotracheal tube cleaning device that can isolate the removed mucus and facilitate easy disposal.

SUMMARY

According to various aspects of the disclosure, an endotracheal tube cleaning device may comprise an elongated member, a cleaning member at a first end of the elongated member, and a collection member. The cleaning member may include a shaving region about a periphery thereof. The elongated member may extend through the collection member, and the elongated member and cleaning member may be slidable relative to the collection member.

In some aspects of the disclosure, a collection device for an endotracheal tube cleaning apparatus may comprise a collection member having a first end and a second end. The first end may comprise an opening configured to slidingly receive an elongated member of an endotracheal tube cleaning apparatus. The opening may include a resilient member cooperating with the elongated member to seal the opening. The second end may be open such that a portion of the tube cleaning apparatus can be extended through the open second end.

According to various aspects of the disclosure, a method of removing mucus accumulations from the inside walls of an endotracheal tube may include inserting a cleaning member into an endotracheal tube, moving the cleaning member relative to said endotracheal tube such that a shaving region of the cleaning member shaves at least one mucous accumulation off the inside wall of the endotracheal tube, and moving the cleaning member relative to a collection member such that the shaved-off mucous accumulation is directed into the collection member.

BRIEF DESCRIPTION OF THE DRAWINGS

FIG. 2 is a side cross-sectional view of the endotracheal tube cleaning device of FIG. 1; and FIG. 3 is an end cross-sectional view of an exemplary collection member of the endotracheal tube cleaning device of FIG. 1.

DETAILED DESCRIPTION

Figure 1:
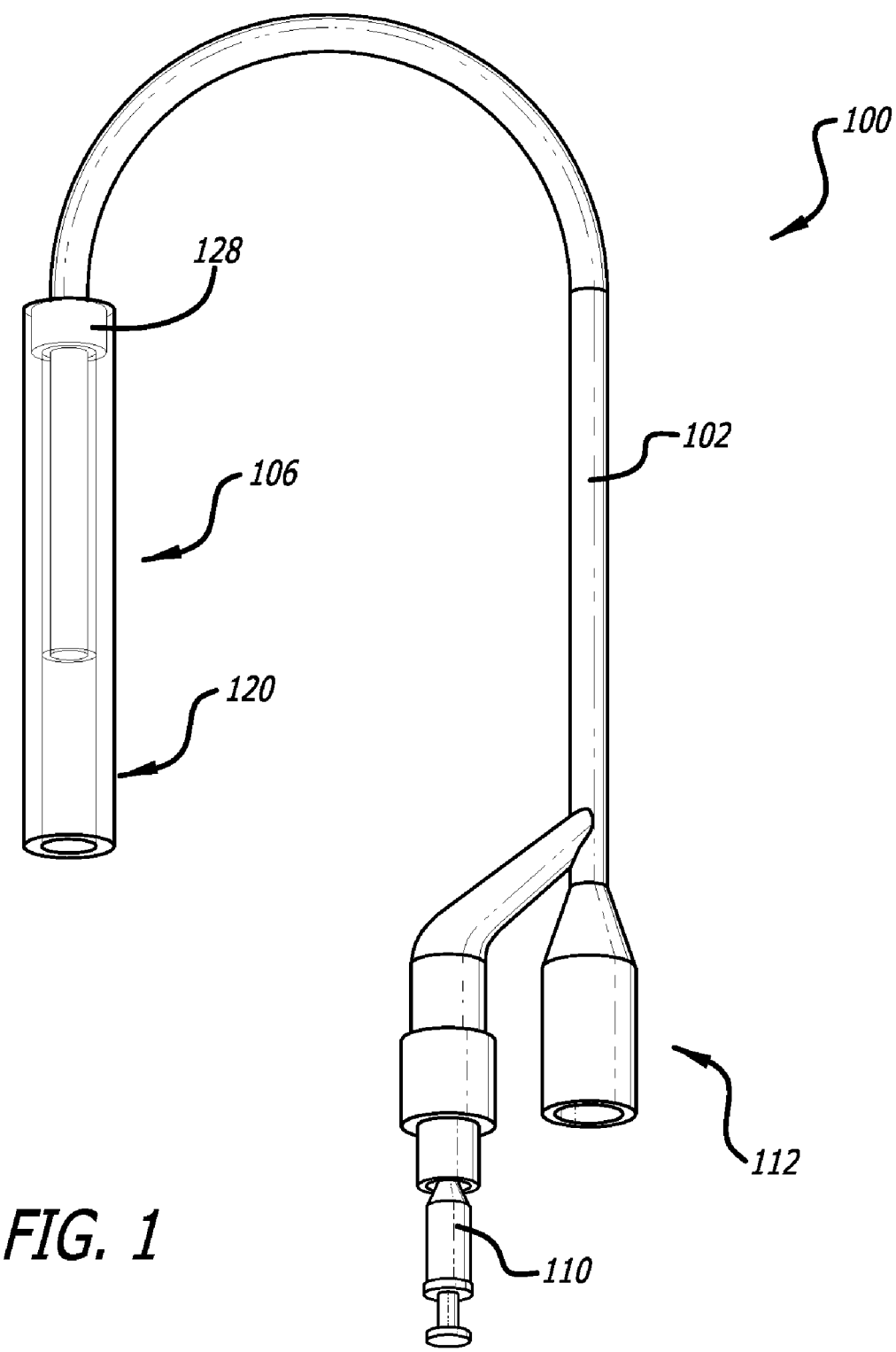
FIG. 1 is a front perspective view of a endotracheal tube cleaning device in accordance with exemplary aspects of the present invention.

The following detailed description should be read with reference to the drawings, in which identical reference numbers refer to like elements throughout the different figures. The drawings, which are not necessarily to scale, depict exemplary embodiments and are not intended to be limiting. This description will clearly enable one skilled in the art to make and use the invention, and describes several embodiments, adaptations, variations, alternatives and uses of the invention, including what is presently believed to be the best mode of carrying out the invention.

An exemplary embodiment of an endotracheal tube cleaning device 100 is illustrated in FIGS. 1 and 2. The endotracheal tube cleaning device 100 may include an elongated member 102 having a first end 106 (e.g., a distal end) and a second end 112 (e.g., a proximal end). The endotracheal tube cleaning device 100 may be structured and arranged for insertion into an endotracheal tube 150 (FIG. 2).

The endotracheal tube cleaning device 100 may include a cleaning member 104 at the first end 106 of the elongated member 102. The cleaning member 104 may have a shaving region 108 about its periphery. The shaving region 108 may comprise at least one shaver 118 about a periphery of the cleaning member 104. Although illustrated in FIG. 2 with three shavers 118, it should be appreciated that the shaving region 108 may include one, two, or more than three shavers.

According to various aspects, the cleaning member 104 may be an inflatable member, such as, for example, a thin-walled balloon tube. The endotracheal tube cleaning device 100 may include an inflation device 110, such as, for example, a syringe, connected to the inflatable cleaning member 104 via the elongated member 102. The elongated member 102 may be structured and arranged to direct fluid from the inflation device 110 to the inflatable cleaning member 104.

The shavers 118 may be formed from a durable elastomeric polymer. The shavers 118 may be configured to shave away a mucus accumulation layer without scraping into the endotracheal tube 150 itself. In some aspects, the inside of the endotracheal tube 150 may have a bactericidal film, for example, which the endotracheal tube cleaning device 100 should leave in place after the mucus accumulation is removed.

According to various aspects, the shavers 118 may be formed integrally with the inflatable cleaning member 104 such as, for example, by injection molding. In some aspects, the shavers 118 may be adhered to the outside of the inflatable cleaning member 104 such as, for example, via an adhesive. According to various aspects, a leading edge 119 (i.e., facing the proximal end 112 of the elongated member 102) of at least one of the shavers 118 may be substantially squared (i.e., an approximately 90° edge) to facilitate removal of mucus accumulation from the endotracheal tube 150.

According to various aspects, the elongated member 102 may be formed of a flexible medical plastic or an elastomer and may be narrow enough in outside diameter so that it does not unduly impede patient ventilation when it is inserted into an endotracheal tube (not shown). Also, the elongated member 102 should be wide enough in internal diameter to quickly inflate the inflatable cleaning member 104 during the cleaning process. For example, an elongated member 102 having a 3.0 mm outside diameter and a 2.0 mm inside diameter can be used, although other sizes and materials would also work. The inflatable cleaning member 104 may be formed, for example, from a durable, easily inflatable elastomeric material such as, for example, silicone rubber.

It should be appreciated that the inflatable cleaning member 104 may comprise any conventional inflatable member and may be inflated in any conventional manner. For example, in various aspects, the inflatable cleaning member 104 may comprise a separate member disposed across a gap in the elongated member 102. The gap may be delimited by two plugs within the elongated member, with one of the plugs having a hole configured to allow inflating fluid to enter the inflatable member. In some aspects, the inflatable cleaning member 104 may comprise a separate member over a region of the elongated member, wherein that region includes through holes to allow fluid flow to inflate the inflatable cleaning member 104. In some aspects, the inflatable cleaning member 104 may comprise a portion of the elongated member 102 with an inflatable chamber limited by plugs or the like.

The endotracheal tube cleaning device 100 may include a collection member 120 slidably coupled with the elongated member 102 and the cleaning member 104. The collection member 120 may have a first end 122 and a second end 124. The first end 122 may include an opening 126 that slidably receives the elongated member 102. The opening 126 may be sized smaller than the cleaning member 104 so that the cleaning member 104, whether inflated or deflated, cannot slide therethrough. As shown in FIG. 3, the opening 126 may comprise a resilient member 128 structured and arranged to cooperate with the elongated member 102 to seal the opening 126 as the elongated member 102 slides relative thereto.

The elongated member 102 may extend through the collection member 120 such that the cleaning member 104 extends beyond the second end 124 of the collection member 120. The second end 124 of the collection member 120 is open such that the cleaning member 104 and/or the elongated member 102 can extend through the open second end 124.

According to various aspects, the collection member 120 may be sized to substantially correspond to an inside diameter of the endotracheal tube 150 so as to enable the inflated cleaning member 104 to be received by the collection member 120. Thus, mucus accumulations shaved by the shaver(s) 118 can be directed into the collection member 120.

According to various aspects, the endotracheal tube cleaning device 100 may include a closure member 130 that can be coupled to the second end 124 of the collection member 120. The closure member 130 may be attached, for example, via a screw fit, friction fit, or the like. The closure member 130 may be used to close the second end 124 when the endotracheal tube cleaning device 100 is removed from the endotracheal tube 150 after cleaning.

It should be appreciated that the inflation device 110, for example, a syringe, should have a sufficient internal volume to fully inflate the inflatable cleaning member 104 against the inside of the endotracheal tube 150. For example, a 10 cc syringe may be used, which allows for inflation and deflation of the inflatable cleaning member 104. According to some aspects, the elongated member 102 may be connected to the patient's ventilation equipment (not shown) to use as an inflation device.

It should be appreciated that the endotracheal tube 150 and/or the endotracheal tube cleaning device 100 may have at least one radiopaque marker 140 for aiding with alignment of the endotracheal tube cleaning device 100 for a cleaning procedure. According to various aspects, at least one radiopaque marker 140 may comprise, for example, a stainless steel anchor.

In operation, the endotracheal tube cleaning device 100, including the collection member 120 may be inserted into an endotracheal tube 150 of a patient. For example, the first end 106 of the cleaning device 100 may be inserted into the proximal end 152 of the endotracheal tube 150. In some cases, the endotracheal tube 150 may need to be disconnected from a ventilation apparatus prior to cleaning. The cleaning apparatus 100 may be inserted into the endotracheal tube 150 such that the shaver(s) 118 of the inflatable cleaning member 104 is substantially coincident with or slightly beyond the distal end 154 of the endotracheal tube 150.

Once the endotracheal tube cleaning device 100 is positioned as desired in the endotracheal tube 150, the inflation device 110 may be used to inflate the inflatable cleaning member 104 until the shaver(s) 118 is pressed substantially flush against the inside surface of the endotracheal tube 150. With the cleaning member 104 inflated, the endotracheal tube cleaning device 100 may be steadily withdrawn proximally relative to the endotracheal tube 150. As the cleaning device 100 is being withdrawn, the leading edge 119 of the shaver(s) will shave off the mucus accumulations and pull them toward the proximal end 152 of the endotracheal tube 150. It should be appreciated that humidified air may be ventilated into the patient so that mucus accumulations can remain moist and removal can be facilitated.

Before the endotracheal tube cleaning device 100 is removed from the endotracheal tube 150, the elongated member 102 is slidingly moved relative to the collection member 120, pulling the shaved-off mucus accumulation, or sputum, into the collection member 120. With the sputum in the collection member, the cleaning device 100 may be removed from the endotracheal tube 150. When the cleaning device 100 is removed from the endotracheal tube 150 after the shaving process is completed, the closure member 130 may be coupled to the second end 124 of the collection member 120. Thus, the sputum may be enclosed and prevented from contacting the physician, nurse, or other practitioner performing the procedure.

It should be appreciated that after each use, the soiled endotracheal tube cleaning device 100 may either be discarded or cleaned and prepared for re-use. According to various aspects, the soiled cleaning device 100 may be immersed in one or more detergent solutions to sequentially clean, rinse, and/or prepare the cleaning device 100 for re-use. According to some aspects, the soiled cleaning device 100 may be discarded since the cleaning device 100 may be relatively simple and inexpensive to manufacture, and avoiding re-use may maintain a high degree of sterility.

It will be apparent to those skilled in the art that various modifications and variations can be made in the medical devices and methods of the present invention without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A method of removing mucus accumulations from the inside walls of an endotracheal tube, the method comprising:
    inserting a cleaning member into an endotracheal tube;
    moving said cleaning member relative to said endotracheal tube such that a shaving region of said cleaning member shaves at least one mucous accumulation off the inside wall of said endotracheal tube;
    prior to removing said cleaning member from the endotracheal tube, moving said cleaning member relative to a collection member disposed inside of said endotracheal tube such that said shaved-off mucous accumulation is directed into said collection member; and
    removing said cleaning member and said collection member from said endotracheal tube.

2. The method according to claim 1, further comprising urging said shaving region of the cleaning member toward an inside wall of said endotracheal tube.

3. The method according to claim 2, wherein said urging comprises inflating said cleaning member.

4. The method according to claim 1, further comprising closing an open end of said collection member upon removal of the collection member from the endotracheal tube.

* * * * *